US012379225B2

(12) United States Patent
Pompili et al.

(10) Patent No.: US 12,379,225 B2
(45) Date of Patent: Aug. 5, 2025

(54) SAFETY-AWARE ROUTE RECOMMENDATION SYSTEM AND METHOD

(71) Applicant: Rutgers, The State University of New Jersey, New Brunswick, NJ (US)

(72) Inventors: Dario Pompili, Hillsborough, NJ (US); Saman Zonouz, Jersey City, NJ (US); Vidyasagar Sadhu, Fremont, CA (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 297 days.

(21) Appl. No.: 17/517,307

(22) Filed: Nov. 2, 2021

(65) Prior Publication Data

US 2022/0136857 A1 May 5, 2022

Related U.S. Application Data

(60) Provisional application No. 63/108,977, filed on Nov. 3, 2020.

(51) Int. Cl.
| | |
|---|---|
| *G16H 50/80* | (2018.01) |
| *G01C 21/00* | (2006.01) |
| *G16H 10/60* | (2018.01) |
| *G16H 50/20* | (2018.01) |
| *G16H 70/60* | (2018.01) |

(52) U.S. Cl.
CPC ........... *G01C 21/383* (2020.08); *G16H 10/60* (2018.01); *G16H 50/20* (2018.01); *G16H 50/80* (2018.01); *G16H 70/60* (2018.01)

(58) Field of Classification Search
CPC ...... G01C 21/383; G16H 70/60; G16H 50/20; G16H 50/80; G16H 10/60
See application file for complete search history.

(56) References Cited

U.S. PATENT DOCUMENTS

| | | | |
|---|---|---|---|
| 6,266,704 B1 * | 7/2001 | Reed | ...................... H04L 45/00 713/153 |
| 11,950,163 B2 * | 4/2024 | Loh | ........................ G08B 21/22 |

(Continued)

FOREIGN PATENT DOCUMENTS

WO    WO-2022058983 A1 *  3/2022

OTHER PUBLICATIONS

Kleinman, Robert A, & Merkle, Colin, Digital Contact Tracing for COVID-19, Jun. 15, 2020, CMAJ (Year: 2020).*

(Continued)

*Primary Examiner* — Matthew L Hamilton
(74) *Attorney, Agent, or Firm* — MEAGHER EMANUEL LAKS GOLDBERG & LIAO, LLP

(57) ABSTRACT

Various embodiments comprise systems, methods, architectures, mechanisms, and apparatus providing location safety management implemented by cooperating mobile devices that operate in a privacy-secured manner to identify respective proximate infectious areas, build corresponding local datasets of the infectious areas, and share the datasets or relevant portions thereof with each other, such as in response to hierarchical location-based requests for such data. The datasets may be used to adapt the operation of navigation applications and the like so as to avoid routes, seats or locations associated with infectious areas and/or persons.

23 Claims, 7 Drawing Sheets

(56) References Cited

U.S. PATENT DOCUMENTS

| | | | |
|---|---|---|---|
| 12,061,721 B1* | 8/2024 | Pala | G06F 21/6263 |
| 2017/0352119 A1* | 12/2017 | Pittman | G16H 50/80 |
| 2018/0052970 A1* | 2/2018 | Boss | G06F 21/35 |
| 2019/0259112 A1* | 8/2019 | Siegman | G06F 16/29 |
| 2021/0257107 A1* | 8/2021 | Hassan | G16H 10/60 |
| 2021/0385614 A1* | 12/2021 | Millius | H04W 4/023 |
| 2022/0051808 A1* | 2/2022 | Miettinen | G16H 50/80 |
| 2022/0115137 A1* | 4/2022 | Goldstein | G16H 10/60 |
| 2022/0178712 A1* | 6/2022 | Marinescu | G16H 10/60 |
| 2022/0285036 A1* | 9/2022 | Merjanian | G16H 50/80 |
| 2022/0290993 A1* | 9/2022 | Miriyala | G06Q 10/0635 |
| 2022/0369925 A1* | 11/2022 | Lord | H04M 1/72457 |
| 2023/0268038 A1* | 8/2023 | Chheng | G16H 50/80 |
| | | | 705/3 |

OTHER PUBLICATIONS

E. Hernández-Orallo, P. Manzoni, C. T. Calafate and J. -C. Cano, "Evaluating How Smartphone Contact Tracing Technology Can Reduce the Spread of Infectious Diseases: The Case of COVID-19,", Jun. 8, 2020, in IEEE Access, vol. 8, (Year: 2020).*

* cited by examiner

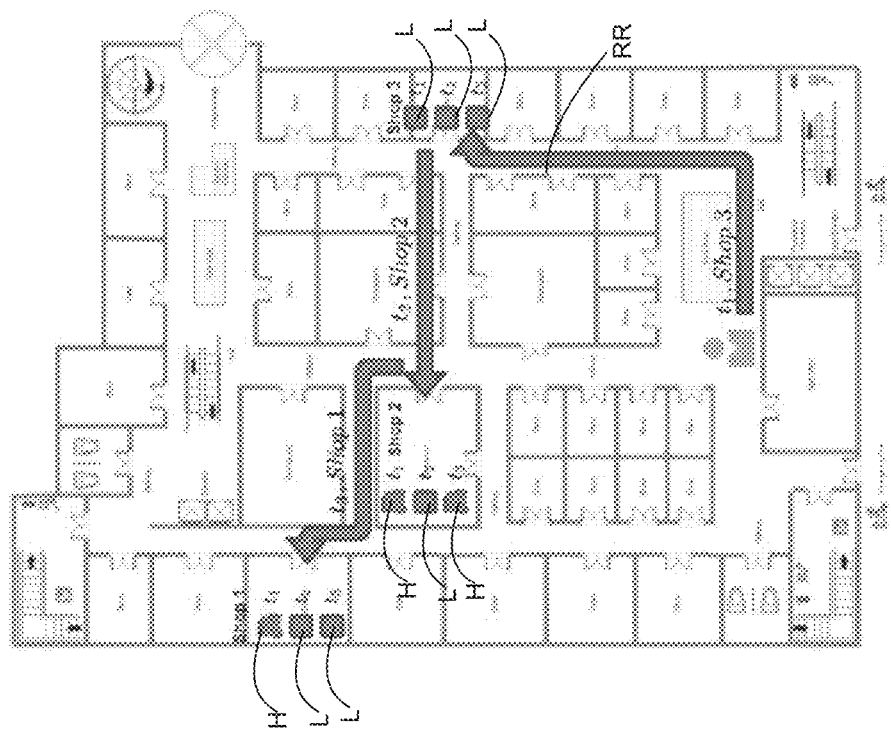
FIG. 4C
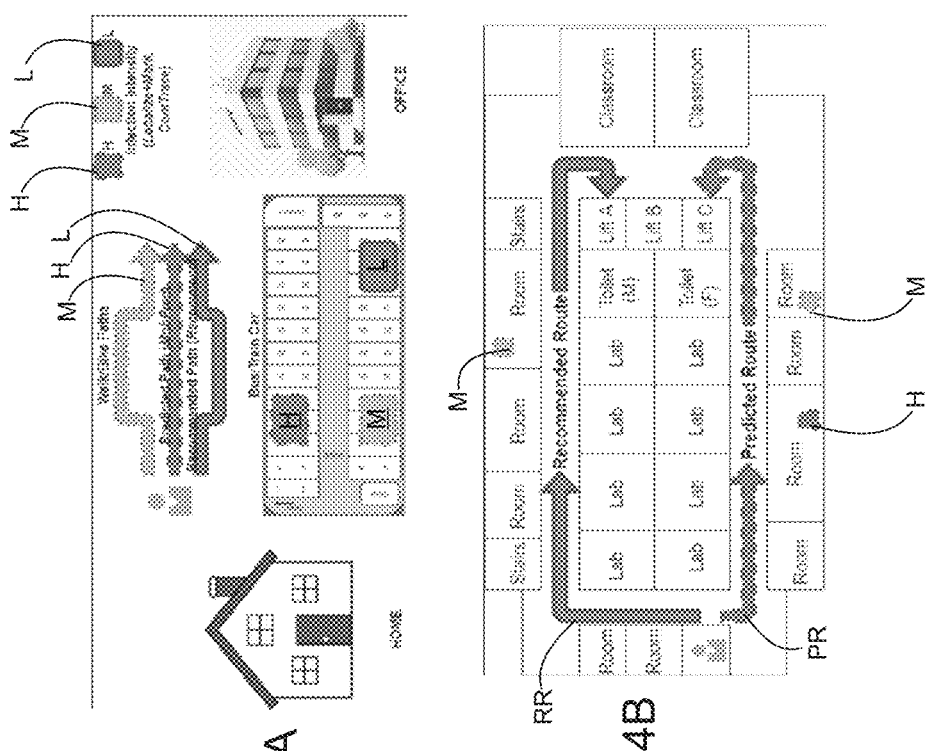
FIG. 4A
FIG. 4B

SAFETY-AWARE ROUTE RECOMMENDATION SYSTEM AND METHOD

CROSS REFERENCE TO RELATED APPLICATION

This application claims the benefit of the filing date of U.S. Provisional Patent Application No. 63/108,977 filed Nov. 3, 2020, the disclosure of which is incorporated herein by reference in its entirety.

FIELD OF THE DISCLOSURE

The present disclosure generally relates to a route recommendation system and, in particular, to a safety-aware location or route recommendation system in which pandemic-related information and other safety contextual information are used to determine routes and route safety levels for indoor and/or outdoor routes.

BACKGROUND

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

COVID-19 is an infectious disease caused by a SARS-CoV-2 virus. It is now known that the SARS-CoV-2 virus spreads primarily through droplets of saliva or discharge from the nose when an infected person coughs or sneezes, and that on average it takes 5-6 days from when someone is infected with the virus for symptoms to show; however, it can take up to 14 days, which is an extremely long period in which asymptomatic people can unknowingly infect relatives, friends, co-workers, and anyone they get close to.

Stopping this new virus will require a large percentage of people to be immune, which will provide indirect protection, or herd immunity, to those who are not immune to the disease. Depending on how contagious an infection is, usually 85% to 95% of a population needs immunity to achieve herd immunity. If SARS-CoV-2 is like other coronaviruses that currently infect humans, it is expected that people who get infected will be immune for months to years, but probably not for their entire lives. If people do not perform physical distancing or enact other measures to slow the spread of SARS-CoV-2, the virus can infect many people in a matter of a few months, which would overwhelm hospitals and lead to high death rates.

It is important for at least the unvaccinated population to maintain some level of continued physical distancing before receiving an effective vaccine. Prolonged effort will therefore be required to prevent major outbreaks. This prolonged effort is required even with a high percentage of the population being vaccinated, since for example there is still a need for vaccine boosters after 6 months along with the possibility of emerging virus variants that are less impacted by the vaccines.

Contact Tracing as a Core Disease Control Measure: contact tracing has been employed by local and state health department personnel for decades as an effective disease-control measure, and is a key strategy for preventing further spread of the COVID-19 pandemic. There are, however, several challenges in the traditional approach—which is based on conducting thorough interviews, cross-referencing documents and data logs, performing laborious tracing and monitoring contacts of infected people as well as notifying them of their exposure—as time is of the essence and immediate action is needed. For these reasons, in order to stop the transmission of COVID-19 it is not sufficient for communities to scale up and follow the traditional approach, e.g., train a large contact tracer workforce and work collaboratively across public and private agencies.

Existing App-based Solutions: several app-based solutions are being developed to track near real time the spread of the COVID-19 disease and to identify which people are likely to be infected based on app users' location history. This is a crucial aspect in order to be able to fully open up the Country's economy again and get people back to work while continuing to protect citizens' lives. An automatic and decentralized privacy-preserving app-based system will reduce patient interview times (which are long, stressful, and often inaccurate) and will contain the spread of the SARS-CoV-2 virus in the population. However, most of the existing solutions have limits, e.g., (i) are reactive in nature in that they detect the exposure after the close contact has happened; (ii) are predominantly Bluetooth-based, which drains battery and raises some privacy and security concerns; (iii) do not give enough consideration to privacy and security aspects; (iv) adopt a centralized approach, which does not scale and is prone to single point of failure; (v) use Global Positioning System (GPS) for location tracking, which does not work indoors.

SUMMARY

Various deficiencies in the prior art are addressed by systems, methods, mechanisms, and apparatus enabling location safety management implemented by cooperating mobile devices that operate in a privacy-secured manner to identify respective proximate infectious areas, build corresponding local datasets of the infectious areas, and share the datasets or relevant portions thereof with each other, such as in response to hierarchical location-based requests for such data. The datasets may be used to adapt the operation of navigation applications and the like so as to avoid routes, seats or locations associated with infectious areas and/or persons.

A location safety management method according to an embodiment comprises receiving indicia of infectious locations proximate the mobile device; adding the received infectious location indicia to an infectious location dataset; in response to receiving a request from another user device for infectious location information within the infectious location dataset, confidentially transmitting at least a portion of the infectious location dataset toward the requesting user device; in response to a need for infectious location information, confidentially transmitting a hierarchically-descriptive infectious location request toward the plurality of cooperating mobile devices; and upon receiving a response to the hierarchically-descriptive infectious location request, adding any received infectious location indicia to the infectious location dataset.

A location safety management system according to an embodiment is implemented at a mobile communication device comprising a processor and a memory for storing computer instructions which, when executed by the processor, cause the mobile device to perform a method comprising: receiving indicia of infectious locations proximate the mobile device; adding the received infectious location indicia to an infectious location dataset; in response to receiving a request from another user device for infectious location information within the infectious location dataset, confidentially transmitting at least a portion of the infectious location dataset toward the requesting user device; in response to a need for infectious location information, confidentially transmitting a hierarchically-descriptive infectious location request toward the plurality of cooperating mobile devices; and upon receiving a response to the hierarchically-descriptive infectious location request, adding any received infectious location indicia to the infectious location dataset.

Additional objects, advantages, and novel features of the invention will be set forth in part in the description which follows, and will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above and with the detailed description of the embodiments given below, serve to explain the principles of the present invention.

FIG. 4A-4C graphically depicts several personal navigation use cases benefitting from the various embodiments;

Figure 1:
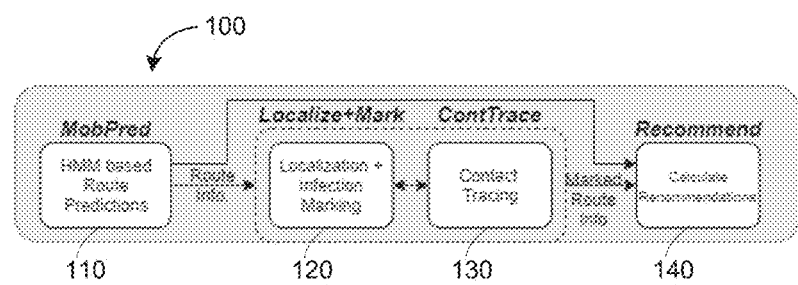
FIG. 1 graphically depicts data flow among several functional elements in accordance with various embodiments.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments.

The various embodiments provide systems, methods, mechanisms, and apparatus providing a location safety management system wherein a mobile device is configured with various modules to perform functions such as identifying or determining infection levels associated with locations proximate the mobile device according to an embodiment, building a corresponding infectious location dataset for local storage, sharing relevant portions of the stored infectious location dataset with other mobile devices, and requesting from other mobile devices any relevant information missing from the stored infectious location dataset. In this manner, applications such as navigation and the like may be configured to avoid guiding the user of the mobile device through infectious locations. Further, the various embodiments contemplate that the sharing of infectious location information and the use of such information is performed in a privacy-preserving manner.

Various embodiments enable personal navigation toward a destination while dynamically generating alternate routes to the destination in response to evolving infection-related threats, such as infected location, the presence of infected people in locations, and so on. Further embodiments provide dynamic location identification and safety classification mechanisms to quickly respond to infection-related threats. Further, various embodiments provide privacy-protection mechanisms to reduce the possibility of inadvertently identifying infected people. The routes may be indoor and/or outdoor routes. For example, various embodiments contemplate spatial aspects such as indoor routes identifying rooms or subregions of a room that could be infectious, and/or outdoor routes that identify places that could be infections. Various embodiments contemplate temporal aspects, such as recommending time periods (i.e., when to visit a particular place and/or when to avoid the particular place), peak times, non-peak times and so on.

The various embodiments provide a *Decentralized Proactive, Predictive, Personalized, Privacy-preserving* (4*P*) COVID-19 recommendation application (i.e., "app") suitable for use in a mobile device (e.g., a mobile phone, tablet or laptop computer, automobile or hand-held navigation system, location enabled watches, and so on) of a user and denoted as the "DP4coRUna" application or app. This mobile device embodiment addresses the following objectives: (1) it is proactive in nature, which helps mitigate the spread of the virus significantly, e.g., it provides recommendations on which path is best to go from place A to B, which regions of the bus/train coach to sit, when to visit which stores in a mall, etc., thereby empowering the user by giving control on what to do and when, so as to minimize the risk of contagion; (2) it is endowed with built-in privacy and security features; (3) it works both indoors and outdoors; (4) it is inherently robust as it is multi-modal because it uses a combination of Wi-Fi Received Signal Strength Indicators (RSSI), cell ID, Location Area Code (LAC), light, sound and/or Geo-magnetic field levels; (5) it is a robust user-based distributed solution; and (6) it achieves high reliability by leveraging collaborative information fusion and model-based verification.

Various embodiments provide a flexible peer-to-peer framework wherein each of several functional modules are implemented at some or all User Equipment (UE) forming a group of UE configured to communicate with each other via a communication network. The UE may comprise mobile communication devices such as mobile phones, tablet or laptop computers, automobile or hand-held navigation systems, location enabled watches, and so on. The UE may be configured to operate in a peer-to-peer manner to collect, store, and share respective location-related safety data such that a relatively comprehensive understanding of location-related safety risks is available to the group of UE for use in avoiding or mitigating such location-related safety risks, such as by augmenting navigation applications to more safely navigate to destination locations.

In various embodiments, substantially all of the safety data collection, storage, sharing is performed by the UE collectively without the need for provider equipment such as servers, databases, and the like.

In various embodiments, a flexible client-server framework is provided wherein some of the functional modules may be implemented at Provider Equipment (PE) such as a location management server, at UE such as mobile communication devices, or via a combination of PE and UE resources.

FIG. 1 graphically depicts data flow among several functional elements of a location safety management system in accordance with various embodiments. Specifically, FIG. 1 depicts an exemplary framework of four functional modules suitable for implementing various; namely, a mobile prediction module 110 (MobPred), a Localize and Mark module 120 (Localize+Mark), a contact-tracing module 130 (Cont-Trace), and a recommendation module 140 (Recommend).

Broadly speaking, the four functional modules interact as follows to enable a user to safely travel from place A to place B (e.g., during a daily commute or for leisure).

The MobPred module 110 builds a model of the user's routine behaviors (both personal and group) in a privacy-preserving manner and predicts the top probable routes taken by the user to go from place A to B (based on historic data).

The model and the building of the model are described in more detail below with respect to the various figures, such as with respect to step 310 and box 315 of the method of FIG. 3, with respect to FIG. 8, and as noted elsewhere herein.

The Localize and Mark module 120 receives the predicted routes information from the MobPred module 110 (or a third-party navigation service such as Google Maps) and analyzes the infection rate of route locations using the location information of the people associated with those routes/locations and also the destination(s). The analysis is performed in a privacy-preserving manner such as via k-anonymity. Specifically, the k-anonymity approach marks a particular location (e.g., a room in a building) to be potentially infectious if at least one person out of k-persons in that location is potentially infected (where "infected" may be defined as presently infected or infected at some time the past 14 days having been in contact with an infected person) as determined using the contact-tracing module 130, which may be implemented by automatically contacting all relevant users as indicated by intersections in time and place with infected individuals, by providing all relevant data to third-party contact-tracing authorities, and so on.

Other factors may be used to indicate that a location is "infected." It is noted that, for privacy reasons, the various embodiments may be configured to avoid identifying which specific person is potentially infected. In various embodiments, the marking of a location as "infected" changes with time as existing persons leave or new persons enter the location. The various embodiments may be configured to indicate a "presently infected" status of a location. The various embodiments may be configured to indicate a reduced infection status of a location, such as via a number of days since an infected person was at the location. Various embodiments contemplate a "persistence" factor or parameter that may be used to define a time-related reduction in an infection level of a location.

The localize and mark functions are described in more detail below with respect to the various figures, such as with respect to step 320 and box 325 of the method of FIG. 3, with respect to FIGS. 4-5 and associated text, and as noted elsewhere herein.

The recommendation module 140 received output data from the mobile prediction module 110, localize and mark module 120, and contact-tracing module 130. The recommendation module 140 responsively generates recommendations to the user on whether to follow an original/prior route or an alternate route, which locations to avoid (e.g., explicitly by indicating the infected locations or implicitly by simply avoiding multiple locations including the infected locations), when to visit a particular destination (such as may be indicated by location markings obtained from the localize and mark module 120). The operation of the various modules will be described in more detail below.

User recommendations are presented to a user via a user device, such as a mobile phone, laptop or tablet computer, automobile navigation system or some combination thereof, such as via Graphical User Interfaces (GUIs) and the like.

Localize+Mark module discussed above provides accurate indoors user localization and, optionally, k-anonymity-based infection marking. The Localize+Mark module first obtains the route information (source and destination) directly from the user or as output of the MobPred module (discussed later below). It then calculates and marks the infectious risk associated with each of these candidate paths/activities using the indoor/outdoor location information of users associated with such paths/activities, optionally using k-anonymity mechanism that preserves user privacy. Indoor/outdoor person localization works without the need for extra infrastructure, other than the already existing Wi-Fi Access Points (WAPs) when based on UE alone. The Localize+Mark module leverages Wi-Fi Received Signal Strength Indicator (RSSI) measurements, which are augmented with additional sensor data such as sound level, light level, cell signal level, Geo-magnetic signal level, etc. to boost the spatial granularity. This also helps in areas with lower WAP density and to distinguish among different regions/rooms within the area covered by a single or set of Wi-Fi APs. While room-level localization granularity of the approach of the various embodiments is understood, the granularity can also be adjusted (finer or coarser) by a parameter called Wi-Fi similarity threshold (assuming that additional sensor data also exhibits feature variability).

Unlike existing indoor localization solutions, various embodiments may provide a pervasive localization solution (i.e., not limited to a single building at a location), which solution may be provided without constructing building maps or identifying important fixtures such as elevators and the like.

The Localize+Mark module tags different locations in and around buildings by a location label using the location-specific signatures/features (such as Wi-Fi APs and their strengths, sound, light, Geo-magnetic, cell signal levels, etc.) as tags.

In addition, privacy as an integral part of some embodiments (rather than an add-on) by using data-perturbation techniques as well as secure connections, such as the cryptographically secure onion routing algorithm derived from The Onion Router (TOR) network for networked smartphones. The use of onion routing or similar privacy-enhanced communications protocols/techniques ensures that the entities that receive an encrypted signal cannot infer information about the signal's past and future routing hops more than the immediate previous and next hops. As the result, the packets' source and destination remain private to other potentially untrusted parties in the middle that are in charge of just receiving and forwarding the packet. To address the issue on reliability, various embodiments obtain location through collaboration from multiple devices. Collaboration not only helps in improving accuracy (by reducing the amount of noise added by virtue of privacy) but also in knowledge sharing from one device to another. It is worth emphasizing that the various embodiments preferably do not use any local collaboration (i.e., collaboration among nearby user devices) as such an approach will likely violate the privacy of other users. Also, it is not necessary that all the people who know about a particular location are present in the vicinity.

Various embodiments use weighted fusion to further improve accuracy. Specifically, to reduce the energy footprint of the hardware/software implementing the embodiments, the various embodiments primarily use Wi-Fi scan data most of the time, which is typically generated by the mobile Operating System (OS) of the UE when the Wi-Fi is ON. On a final note, the embodiments are scalable as each device stores the location data (which may be time-stamped and/or anonymized) it is associated with (i.e., visited at some point of time) and nothing else. For example, if a device has never visited a certain place, then its database will never contain entries corresponding to that place. Existing work on contact tracing using phone pairing are location agnostic; therefore, 'hub' regions (e.g., train stations) would not be recognized blindly as risky places. After Localize+Mark localizes the users in a privacy-preserving manner, it marks/ tracks the location in terms of how infected each place may be (using k-anonymity mechanism) based on the infection-state of the people who are there or have been recently.

ContTrace module determines people who have been there recently, where the database entries of two devices are compared to find a similarity match. Existing contact-tracing solutions are state-less and hence cannot predict where the user may go next. ContTrace identifies the people who had been in contact with a particular person or location (say 'specimen') in the past two weeks, which is accomplished as follows. The database records (i.e., the locations and their sensor signatures) of specimen corresponding to the last two weeks are queried over the TOR network to identify devices whose databases have matching information in the last two weeks. When a device receives these query records, it initiates a comparison check to see if any of the query records are similar to the records in its database. If it is so, then the app alerts the user that s/he had been in potential contact with an infected person in the past two weeks and suggests the user to self-quarantine and contact the health provider. When this happens the app also presents the matching records (with sensor signatures including Wi-Fi, Cell ID, etc.) in its database that are similar with the query for user validation. It is noted that this software module can be replaced with other existing solutions, e.g., Apple/Google app if needed, while still reaping the benefits of the other three modules.

MobPred module of the app on each user's phone (without any data disclosure to external parties, e.g., clouds) models the user's recent location trajectories within the building. Such accurate behavioral profiles enable the various embodiments to predict the user's next destinations, which is required for effective proactive advisory. MobPred can predict the user's next potential destinations and advise accordingly (e.g., go, wait, or don't go) given the current status of that specific destination and its occupying individuals (and their past locations and contacts). MobPred builds a model of the user's personal and groups behaviors (observed with contextual attributes such as location, time, apps running on the phone, people around the phone, etc.) so as to predict the top-most probable paths/activities undertaken by the user. The main advantages of MobPred are as follows: by predicting the activities ahead of time, it gives extra lead time to the user to plan his/her schedule in a flexible way; can advise on when to do the predicted activities for reduced exposure, e.g., if the prediction is to go to place A at noon tomorrow, but if it is known that the infection is high at that time, it can advise to go at 10 am instead. MobPred first builds a personalized model (Self-Context) that predicts the user's context based on its past sequential history of contexts. Obtaining context from personalized model adds an extra layer of confidence to the context obtained directly from phone sensors. However, the following situations are possible: contexts obtained from both approaches are very different, contexts from one of the approaches is not available (e.g., GPS may not be available from phone sensors indoors, etc.) or insufficient leading to uncertainty. In such situations, assuming the user is closely connected to a group of people (e.g., same team, colleagues in the company, gym friends, family members, etc.), it is possible that the context of other members in that group of people can provide additional information about his/her context. For example, assume users A and D often go to lunch together (learned via model). Now somehow if it is known that D is going to "Restaurant 1" tomorrow for lunch, it is most likely that the context of user A tomorrow around 1 pm is "having lunch with D at Restaurant 1" without having to rely on A's phone sensors at that instant. The various embodiments address this aspect of context to provide a second layer of confidence to the context (over and above the personalized model). For this purpose, the various embodiments use such context obtained through collaborative filtering of the contexts of users closely related to the primary user (GroupContext). Such collaborative filtering for mobile contexts can be used to validate and/or enhance the current context obtained from sensors or predict the future context for proactive advisory. Various embodiments utilize a privacy-preserving method for parameter estimation (training) of GroupContext, as users may not be willing to share their private data with each other.

Recommend, the last and final module, then takes the outputs of the previous modules to generate the top recommendations for the user in decreasing order of strength. Recommend models the problem as an optimization problem and solves it b y leveraging state-of-the-art combinatorial optimization techniques. A simple approach for this would be as follows. Recommend first gathers the route/place information along with the intensity markings obtained from previous modules. It then tries to find all the possible combinations satisfying the problem at hand (e.g., all routes from place A to place B), along with their combined average marking intensity and any additional cost information (i.e., time taken to follow the route). It then displays all possible solutions in decreasing order of marking intensity (e.g., using three colors such as red, green, and blue) along with additional cost information such as time taken to follow the route. The user can then choose the option that best fits his/her requirements. In this way, the various embodiments provide the users with valuable information and put the users in a position to make the best decision for themselves.

FIG. 4 graphically depicts several personal navigation use cases befitting from the various embodiments. In particular, FIG. 4 depicts three of the many use cases benefiting from the various embodiments; namely, (1) a mixed outdoor-indoor navigation from place A (e.g., home) to place B (e.g., office) via both walking/biking and public transportation (e.g., bus or train modes); (2) indoor navigation within a shopping mall (e.g., as an entertainment or leisure activity); and (3) indoor navigation within an office/university location (e.g., as a work activity). In each of these use cases different colors may be used to represent respective differences in intensity of infection at the relevant locations; for example, red, orange, and green may be used to indicate the intensity of infection (in decreasing order) as well as the strength of the recommendations (green indicating the best recommendation). In various embodiments, colors may be replaced with or augmented using different line styles, such as with dashed, dotted, and solid lines to represent, respectively, red, yellow, and green infection intensities/recommendation strengths. In various embodiments, each color can be split into two shades (e.g., darker and lighter color variants) to further realize a higher granularity and achieve a total of six colors for marking and recommendation. Referring to FIGS. 4A-4B, it can be seen by inspection that seating locations such as on a bus or train, predicted routes (PR) and recommended routes (RR) are depicted, which locations/routes are defined in response to locations having high (H), medium (M) or low (L) infection intensity levels.

Various embodiments use an infectious location dataset stored at a mobile device and periodically updated to adapt the operation of a navigation application to reduce a number of infectious locations associated with a recommended route. Such adaptation may comprise an integration with the navigation application to include infectious location information as part of the route calculation performed by the navigation application. Such adaptation may comprise identifying specific infectious areas associated with a recommended route such that a user may avoid traversing such areas while following the recommended route, which may further lead to route updates via the navigation application.

Further embodiments contemplate generating an alert indicative of a recommended route including an infectious location, a current user location being proximate an infectious location, and/or other conditions indicative of a heightened danger to the user.

Various embodiments use an infectious location dataset stored at a mobile device and periodically updated to adapt the operation of a navigation application to identify infectious locations such as seats in a car, bus, train, plane, or other public conveyance. Relevant alerts such as those discussed herein may also be generated.

FIG. 4A graphically depicts a first use case; namely, a mixed outdoor-indoor scenario that is common in daily commutes, where a traveler wants to go from home to workplace (e.g., an office). MobPred first identifies the type of mode that a user/traveler usually takes and calculates the top probable paths. In case it is walk/bike, Localize+Mark identifies the infection markings along the Bob's probable paths utilizing the ContTrace module to check infection history in the past 14 days. Recommend then recommends the safest and best path for the user/traveler to take in order to avoid getting infected and reach the workplace in the least amount of time. From the figure, it can be seen that the most probable route predicted by MobPred is the shortest one, but is also marked infectious by Localize+Mark (in red). Hence, Recommend recommends a slightly longer path (indicated in green) as it is the safest. In case the predicated mode of travel is public transport, it may be argued that that carpooling is not safe (due to close contact between passengers, less than 6 feet, and recirculated air); hence it has to be either a bus or a train. In either case, Localize+Mark in the app shows the user potential infected areas within the coach at the current moment and the recent past (using the ContTrace module). Recommend then calculates and displays the best and safest sitting regions for the user within the coach so as to minimize possible contagion.

FIG. 4B graphically depicts a second use case; namely, a shopping mall (entertainment-related indoor scenario), where the user's goal is to visit three shops indicated on the figure. Localize+Mark calculates the markings for the three shops at times t1, t2, and t3. It is seen here that Shop 1 is marked infectious at t1, but not so at times t2, t3; the various embodiments can have similar such data for the other two shops. Recommend then generates the recommendations for the user/traveler as to which shop to visit and at what time, thereby solving the know "Traveling Salesman Problem" (TSP—a classic algorithmic problem in computer science and operations research field). From the figure, it can be seen that Recommend recommends times t3, t2, t1 for the user to visit shops 1, 2, 3, respectively (indicated in green). However, after the user is done with Shop 3, the markings for the remaining shops might have changed re-triggering TSP again if needed (i.e., if the markings have changed).

FIG. 4C graphically depicts a second use case; namely, an office location (work-related indoor scenario). Here, the user's goal is to exit from his room and take the elevator. As an example, an app according to the various embodiments may not recommend taking an elevator in a current time period if there are already people inside the elevator such that it will be hard to keep 6 feet of physical distance. For example, if the elevator is empty, the air in it does not pose a risk unless some very particular event just happened there that generated aerosols, e.g., inserting a tube into an airway, vomiting, etc. That is, there is a persistence or time-based reduction or mitigation of a risk-related event. MobPred calculates the most probable paths usually taken by Bob. Localize+Mark calculates the infection risk associated with each path (i.e., rooms along the path) as in the first use case. From FIG. 4C it may be seen that the most probable path (Predicted Route PR, which may be displayed as a red path), even though it is the shortest, is riskier due to certain rooms along that route being marked infectious by Localize+Mark. Hence, Recommend suggests a longer yet safer route (Recommended Route RR, which may be displayed as a green path) for the user/traveler to follow to reach the elevator.

As previously noted, the various embodiments provide a flexible framework wherein several functional modules are implemented at Provider Equipment (PE) such as a location management server, implemented at User Equipment (UE) such a mobile communications device (e.g., a mobile phone, tablet or laptop computer, automobile or hand-held navigation systems, location enabled watches, and so on), or implemented via a combination of PE and UE resources.

Figure 2:
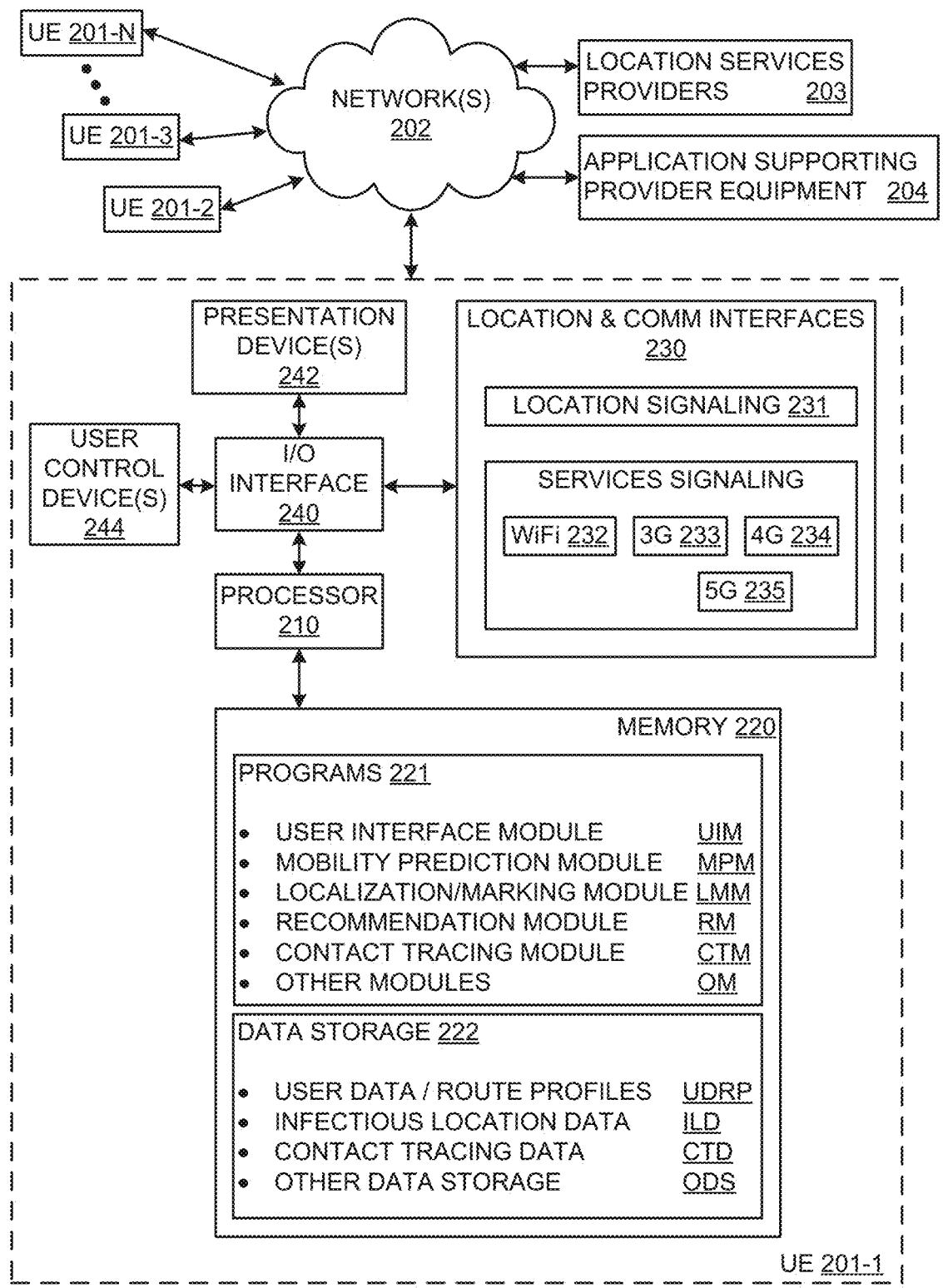
FIG. 2 depicts a high-level block diagram of User Equipment (EU) suitable for implementing a location safety management system according to an embodiment.

FIG. 2 depicts a high-level block diagram of UE suitable for implementing a location safety management system according to an embodiment. Specifically, FIG. 2 depicts a location safety management system 200 comprising a plurality of UE denoted as UE 201-1, 201-2, 201-3, and so on up to 201-N (collectively UE 201) connected to and receiving various network services from one or more networks 202. The system 200 of FIG. 2 optionally includes one or both of locations services provider servers 203 and application supporting provider equipment 204.

The one or more networks 202 may comprise a communications or networking infrastructures including, illustratively, one or more Local Area Networks (LANs), Wide Area Networks (WANs), access networks, core networks, mobile telecommunication networks, Wireless Access Points (WAPs), and/or other devices supporting an appropriate communications infrastructure. It will be appreciated that the communications infrastructure may comprise various other technologies depending on distance, environmental factors, and the like as is known to those skilled in the art (e.g., Bluetooth, 802.11x, Wi-Fi, WiMAX, 3G, 4G/LTE, 5G, etc.). Portions of networks 202 may comprise optical, satellite or other network infrastructure to support communications between the various UE 201, and between the UE 201 and any locations services provider servers 203 or application supporting provider equipment 204.

Location-service provider servers 203 may comprise, for example, those providing/enabling location services for providing routes/directions between source and destination, such as for Google Maps, Microsoft Maps, and the like. Application supporting provider equipment 204 may comprise, for example, equipment enabling the graphical overlaying or combination of additional, user-helpful visual information with the other information discussed herein, such as infectious disease or other public health related information from third party sources (e.g., hot zones, infection rates, testing locations and so on associated with COVID-19, flu, etc. such as provided by Universities, news aggregators, government agencies and the like), weather information, or other useful contextual information from around the web or via directly linked sources.

The UE 201 of FIG. 2 is configured for location related services such as mapping, routing, and other location related services and, as such, includes location monitoring equipment or sensors suitable for determining user location such as via GPS, Radio Frequency (RF) identification systems (e.g., indoor identification of WAPs, location beacons and the like), RF tagging system (e.g., indoor or outdoor location tags, door scanners and the like), information received from indoor or outdoor security devices (e.g., proximity sensors and the like), information received from other mobile devices (e.g., via blue-tooth recognition/query of other mobile devices), and so on.

The UE 201 may be configured for use as part of a group of UE forming a peer-to-peer framework or network of UE wherein some or all of the functional modules described herein are implemented at some or all UE forming the framework or network of UE. The UE may comprise mobile communication devices such as mobile phones, tablet or laptop computers, automobile or hand-held navigation systems, location enabled watches and so on. The UE may be configured to operate in a peer-to-peer manner to collect, store, and share respective location-related safety data such that a relatively comprehensive understanding of location-related safety risks is available to the group of UE for use in avoiding or mitigating such location-related safely risks, such as by augmenting navigation applications to more safely navigate to destination locations.

In various embodiments, substantially all of the safety data collection, storage, sharing is performed by the UE collectively without the need for provider equipment such as servers, databases, and the like.

In various embodiments, the UE 201 provides a GUI configured to enable user interaction (e.g., such as with a mapping/routing application as well as user interactions in accordance with the various embodiments) by, illustratively, displaying current mapping/routing information based upon a graphical representation of at least a portion of a current route being traveled by the user (e.g., such as depicted with respect to FIGS. 4A-4C).

As depicted in FIG. 2, UE 201-1 is broadly representative of the other UE 201 and includes a processor 210, a memory 220, communications interfaces 230, input-output (I/O) interface 240, presentation interface(s) 242, and user control devices 244. The processor 210 is coupled to each of memory 220, location and communication interfaces 230, and I/O interface 240. The I/O interface 240 is coupled to presentation interface(s) 242 for presenting information on UE 201 (e.g., mobile phone display screen, tablet display screen, laptop display, navigation device display, watch or other wearable device display and the like) and is coupled to user control interface(s) 244 (e.g., mobile phone touch screen, tablet touch screen, laptop touchscreen, keypad input devices, microphones, light sensing devices and the like) for enabling user control of UE 201.

The processor 210 is configured for controlling the operation of UE 201, including operations to provide the dynamic mapping/routing capabilities discussed herein with respect to the various embodiments.

The memory 220 is configured for storing information suitable for use in providing the various functions described herein with respect to the embodiments, such as providing mapping, marking, dataset construction, storage, and transmission functions, dynamic mapping/routing capabilities and so on as discussed herein with respect to the various embodiments. The memory 220 may store programs 221, data 222, and the like.

In one embodiment, programs 221 may include programming modules/routines such as a user interface module UIM (e.g., a graphical user interface) suitable for use in supporting user input and display functions. Further, the programs 221 may include one or more programming modules/routines such as a mobile prediction module MPM, a Localize and Mark module LMM, a contact tracing module CTM, and a recommendation module RM, and other modules OM suitable for use implementing the various functions described herein with respect to the embodiments.

In various embodiments, data storage 222 may include one or more databases, file storage mechanisms and the like such as, illustratively, user data/route profiles UDRP, infection location data ILD (which may be time-stamped and/or anonymized), contact-tracing data CTC and other data storage ODS. The memory 220 may store any other information suitable for use by UE 201 in supporting the various functions described herein with respect to the embodiments. For example, the data storage 222 may be used to store an entire database of location-based infectious risk information, or datasets of partial information (e.g., relevant only to locations of recent, current, and/or future interest to the UE) and so on, such as described below with respect to FIG. 3.

The communications interfaces 230 include a location signaling interface 231 configured to support location related services such as mapping, routing, and other location related services. For example, various embodiments include location monitoring equipment or sensors suitable for determining user location such as via GPS, RF identification systems (e.g., indoor identification of WAPs, location beacons and the like), RF tagging system (e.g., indoor or outdoor location tags, door scanners and the like), information received from indoor or outdoor security devices (e.g., proximity sensors and the like), information received from other mobile devices (e.g., via blue-tooth recognition/query of other mobile devices), and so on.

The communications interfaces 230 include one or more services signaling interface such as a Wi-Fi or WiMAX interface 232, a 3G wireless interface 233, a 4G/LTE wireless interface 234, and/or a 5G wireless interface 235 for supporting data/services signaling between UE 201 and external communications and services infrastructure/network 106. It will be appreciated that fewer or more, as well as different, communication interfaces may be supported.

The I/O interface 240 provides an interface to the presentation device(s) 242 and user control device(s) 244 of UE 201. The presentation device(s) 242 may include a mobile phone, tablet computer or laptop computer display screen, and the like, which may be used for displaying data, displaying video, playing audio, and the like, as well as various combinations thereof. The typical presentation interfaces associated with user devices, including the design and operation of such interfaces, will be understood by one skilled in the art. The user control device(s) 244 may include any user control interface(s) suitable for use in enabling a user of the UE 201 (e.g., a patient navigating a building at a medical complex) to interact with the UE 201 and communicate thereby with other UE 201 or provider equipment via the network infrastructure 202. For example, the user control device(s) 244 may include touch screen-based user controls, stylus-based user controls, a keyboard and/or mouse, voice-based user controls, and the like, as well as various combinations thereof. The typical user control interfaces of user devices, including the design and operation of such interfaces, will be understood by one skilled in the art.

Although primarily depicted and described as having specific types and arrangements of components, it will be appreciated that any other suitable types and/or arrangements of components may be used for UE 201. The UE 201 may be implemented in any manner suitable for enabling interaction with a load manager such as to select or admit patients to a load plan being formed, locate the patients in a transport platform, allocate resources to the patients and/or for other functions as described herein.

It will be appreciated that the functions depicted and described herein with respect to the UE 201 may be implemented in hardware and/or a combination of hardware and software, e.g., using a general-purpose computer, one or more application specific integrated circuits (ASIC), and/or any other hardware equivalents. In one embodiment, the various programs depicted as loaded within memory 220 are executed by the processor(s) 210 to implement their respective functions. It will also be appreciated that the various programs may be stored on a computer readable storage medium prior to being loaded into memory 220; such computer readable storage media comprising semiconductor memory devices, magnetic media, optical media, electromagnetic media and the like. Generally speaking, any form of tangible and non-transient computer memory may be used to store computer instructions which, when executed by the processor 210, operate to perform the various methods and functions described herein.

It is contemplated that some of the steps discussed herein as software methods may be implemented within hardware, for example, as circuitry that cooperates with the processor to perform various method steps. Portions of the functions/elements described herein may be implemented as a computer program product wherein computer instructions, when processed by a computer, adapt the operation of the computer such that the methods and/or techniques described herein are invoked or otherwise provided. Instructions for invoking the inventive methods may be stored in tangible and non-transient fixed or removable media, transmitted via a data stream in a tangible and non-transient signal-bearing medium, and/or stored within a memory within a computing device operating according to the instructions.

In various embodiments, all of the programs 221 are implemented in the UE 201. In various embodiments, some of the programs 221 are implemented in the provider equipment 204 and some of the programs 221 are implemented in UE 201. In various embodiments, the programs 221 are implemented in a combination of provider equipment 204 and UE 201. The various modules/routines may be combined as will be discussed in more detail below.

Figure 3:
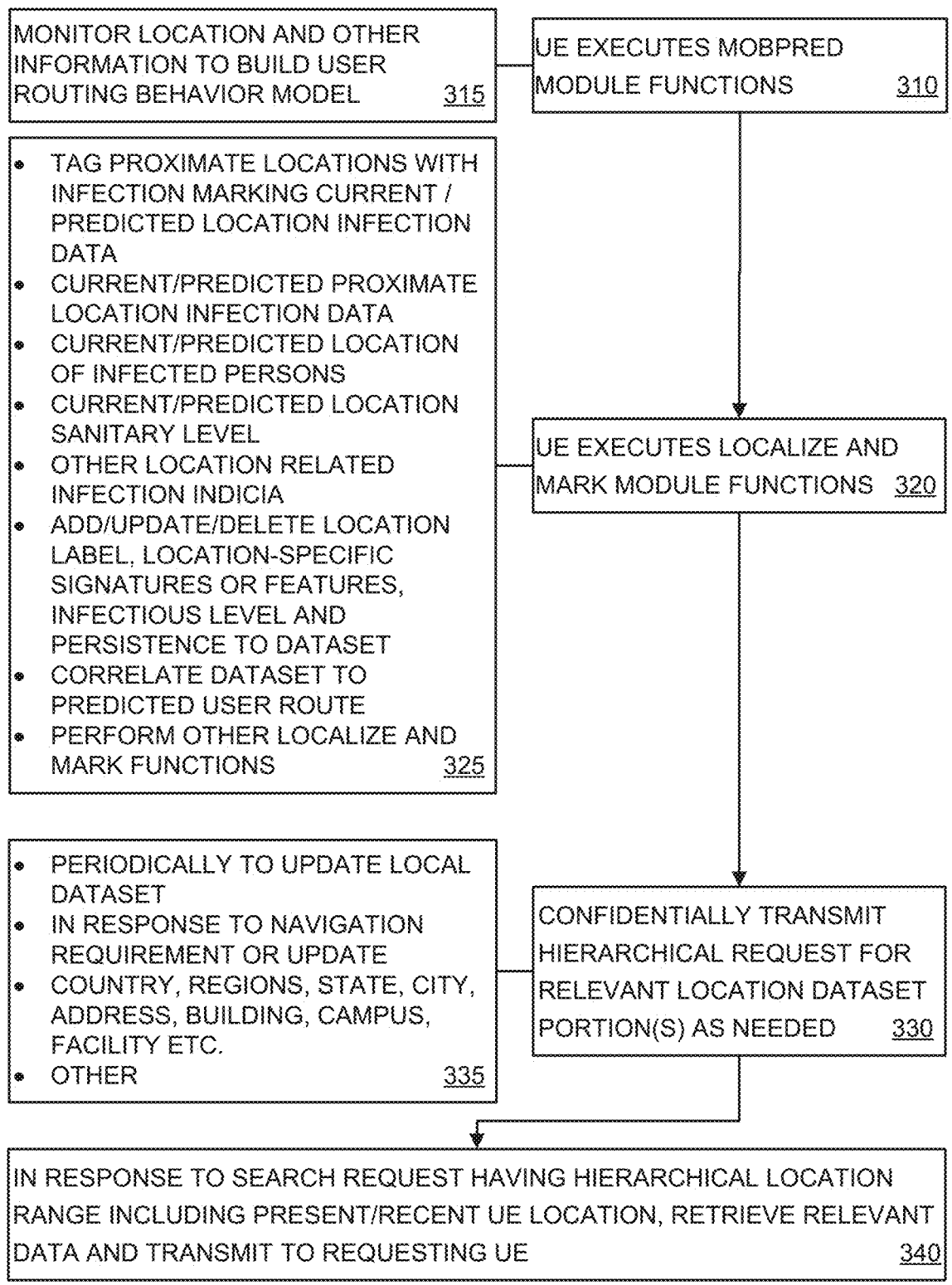
FIG. 3 depicts a flow diagram of a distributed dataset updating and sharing method according to an embodiment.

FIG. 3 depicts a flow diagram of a distributed dataset updating and sharing method according to an embodiment. Specifically, the method 300 may be implemented at UE 201 in whole or in part as previously noted. Generally speaking, the method 300 of FIG. 3 contemplates that all or most of the UE 201 within a group of UE sharing infectious location data (which may be time-stamped and/or anonymized) perform various functions on a frequent basis as the UE location changes. Such functions include monitoring current location information and related infectious levels to keep a dataset as up to date as possible, sharing that dataset or portions thereof with other UE, and using the dataset (updated if needed) to implement various functions by UE apps, such as navigation functions configured to use the dataset to avoid infections hot spots.

At step 310, the UE executes the various MobPred module functions, illustratively in a background or threaded mode of operation. That is, and referring to box 315, the UE operates to continually monitor the location of the UE and other information to build a user routing behavior model and perform other MobPred related functions as discussed herein.

At step 320, the UE executes a portion of the various Localize+Mark module functions, illustratively in a background or threaded mode of operation. That is, and referring to box 325, the UE operates to tag locations with infection related indicia such as marking current or predicted location-based infection data, current or predicted proximate location infection data (i.e., data associated with locations proximate or adjacent to the identified intermediate locations), current or predicted locations of infected persons, current or predicted sanitary levels of the intermediate locations, and special or other location related infection indicia.

Further, an infection location dataset is updated to add/update/delete location label(s), location-specific signatures or features, infectious level and persistence information as is available. Further, the infection location dataset may be correlated to a predicted or currently mapped user route and/or used to perform other localize and mark functions.

As previously noted, the Localize+Mark function is configured to mark relevant paths/locations with infection intensity (e.g., in a k-anonymous manner) based on the localization information of persons (obtained preserving privacy) associated with these paths/locations. The various embodiments implement a privacy-preserving localization framework, which works both indoor and outdoor without relying on GPS signals, and further provide an infection-marking solution.

As previously noted, a first component of the Localize portion involves each device building a local location database (or group of relevant datasets), consisting of multi-modal location features (such as Wi-Fi SSID strengths, Cell ID, Location Area Code (LAC), sound and light levels, etc.) and location labels (e.g., Meeting Room A, Room 203, etc.); the labels are predominantly acquired from collaboration sessions instead of manual input.

At step 330, the UE confidentially transmits a hierarchical request for relevant location dataset portions as needed. Referring to box 335, the locally stored dataset may be periodically updated, may be updated in response to a navigation requirement such as an update or newly selected route or destination, or other application related requirement. The hierarchical search may comprise a request for dataset updates be sent to at least all UE matching the hierarchical criteria, such as country, regions, state, city, address, building, campus, facility, and the like. In various application, finer or coarser granularities of hierarchical criteria may be used.

As previously noted, a second component of the Localize portion involves the location requester contacting the location providers in a secure and privacy-preserving manner such as via a network using The Onion Router (TOR) protocol, or via some other secure means of communications.

At step 340, in response to the UE receiving a search request having a hierarchical location range including the present and, optionally, recent UE location, the UE retrieves at least the search-relevant portions of its dataset and transmits the information to the requesting UE or other device. That is, if the UE is a collaborator device with respect to another UE needing and requesting relevant dataset or database information, the UE transmits the relevant portions of its stored dataset to the requesting UE.

As previously noted, a third component of the Localize portion involves two parts; namely, (a) the location features provided by the requester are queried against the location databases of location providers using a two-step classification procedure; this also identifies the devices (called collaborators) that have some location information about the request; and (b) the outputs of the collaborators are fused using weighted fusion to filter out noisy devices and to generate the final location distribution, which is then sent back to the requester. These components are expanded below.

Figure 5:
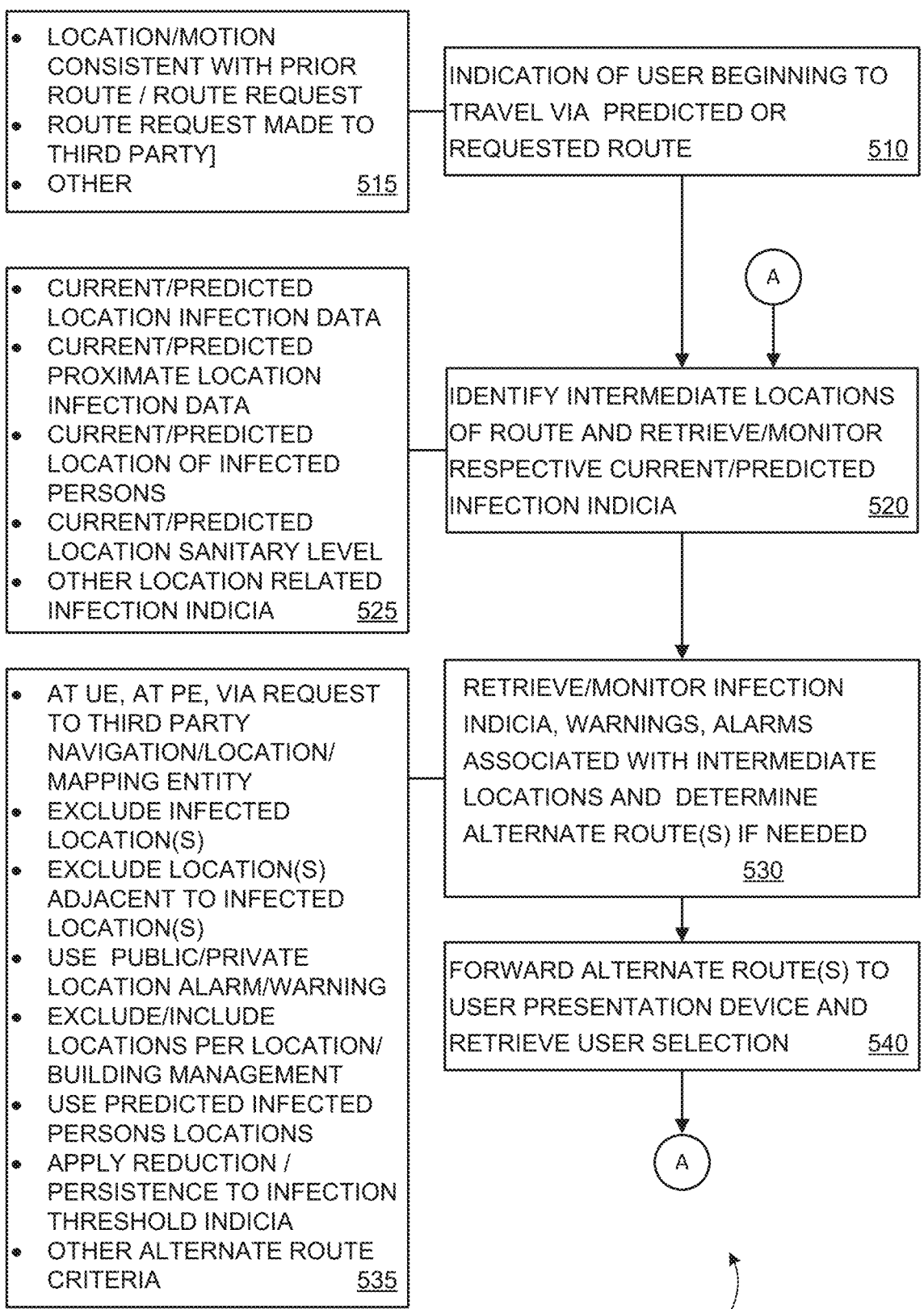
FIG. 5 depicts a flow diagram of a dynamic route recommendation method according to an embodiment.

FIG. 5 depicts a flow diagram of a dynamic route recommendation method according to an embodiment. Specifically, the method 500 may be implemented at UE 201 in whole or in part as previously noted. As such, various portions of the method 500 as discussed are applicable to functions implemented at UE 201, and/or other entity suitable for use in practicing the methods or portions thereof as described herein.

At step 510, an indication of user travel via a predicted or requested route is received. Referring to box 515, the indication may comprise location/motion consistent with a prior traveled route or prior route request, or with a current route request such as provided via at third party navigation or mapping service.

At step 520, intermediate locations of the routes are identified and infection this year associated with these locations is retrieved and/or monitored. If predicted infection indicia is available, then this may also be retrieved. Referring to box 525, infection indicia may be provided via current or predicted location-based infection data, current or predicted proximate location infection data (i.e., data associated with locations proximate or adjacent to the identified intermediate locations), current or predicted locations of infected persons, current or predicted sanitary levels of the intermediate locations, and special or other location related infection indicia. Further, data may be "pre fetched" from other users confidentially transmitting a hierarchically-descriptive infectious location request toward other users' cooperating mobile devices, such as if current user movement is associated with a route defined within the routing behavior model.

At step 530, infection indicia, warning, alarms and the like associated with the intermediate locations is retrieved and/or monitored to determine whether one or more alternate routes are needed (i.e., routes avoiding infected locations).

Referring to box 535, determination of the need for one or more alternate routes, as well as generation of such alternate routes, may be performed at UE, PE, or via request to a third-party navigation, location or mapping entity. Further, alternate routes may be generated by determining/requesting a new route to the destination where infected locations and, optionally, locations adjacent to infected locations or excluded (i.e., force remapping of route without excluded locations or locations adjacent thereto).

Further, excluded locations may also comprise those locations associated with a public or private warning or alarm, such as provided via the management of the building or venue (e.g., infected or closed rooms, ingress/egress means, and other indoor location or after locations).

Further, excluded locations may also comprise those locations where one or infected persons are located or predicted to be located at the time the user is scheduled to traverse the location.

Further, a level of infection associated with a location may be reduced over time by applying a "persistence" value to the location, such as deeming a location to be on infected two days or 12 hours or some amount of time after an infected person has vacated the location.

Further, other alternate routes criteria may be applied.

At step 540, the one or more alternate routes are forwarded to the user's presentation device to enable thereby user selection of an alternate route.

In various embodiments, the method continually repeats steps 520-540 while the user is engaged in travel to the route destination.

Further Discussion of Modules

Localize+Mark marks the relevant paths/locations with infection intensity (in a k-anonymous manner) based on the localization information of persons (obtained preserving privacy) associated with these paths/locations. The various embodiments implement a privacy-preserving localization framework, which works both indoor and outdoor without relying on GPS signals, and further provide an infection-marking solution.

The Localize portion may divided into three components. The first one involves each device building local location database (which may comprise location data that is time-stamped and/or anonymized), consisting of multi-modal location features (such as Wi-Fi SSID strengths, Cell ID, Location Area Code (LAC), sound and light levels, etc.) and location labels (e.g., Meeting Room A, Room 203, etc.); the labels are predominantly acquired from collaboration sessions instead of manual input. The second component involves the location requester contacting the location providers in a secure and privacy-preserving manner such as via a network using The Onion Router (TOR) protocol, or via some other secure means of communications. The third component consists of two parts: in the first, the location features provided by the requester are queried against the location databases of location providers using a two-step classification procedure; this also identifies the devices (called collaborators) that have some location information about the request. In the second, the outputs of the collaborators are fused using weighted fusion to filter out noisy devices and to generate the final location distribution, which is then sent back to the requester. These components are expanded below.

It is assumed that all rooms have publicly-known names and all participants using the various embodiments are aware of the names. A location label (consisting of publicly-known room name, building name, and address) is associated with a set of tags such as the list of Wi-Fi access points at that location in signal-strength order, cell tower ID, cell signal strength, light level, sound level, geo-magnetic signal, which may be denoted together location features. Location features other than Wi-Fi may be used to further distinguish regions covered by a single Access Point (AP), or set of APs. An entry is defined as the location features and its location label. The application maintains these entries in its database and adds new entries based on a similarity metric. The procedure to add entries to the database is as follows. The application listens for the Wi-Fi scan results (list of APs and their signal strengths) generated by the OS (when user turns off Wi-Fi, the app itself requests scans while in other cases it uses the results of scans initiated by the OS or other apps).

A similarity measure between two lists of APs is defined as follows:

$$sim = \frac{\sum_{k=1}^{m}\sum_{j=1}^{n} AP_i^{(a)} AP_j^{(b)} \delta_{ij}}{\sqrt{\sum_{k=1}^{m} AP_i^{(a)2}} \sqrt{\sum_{j=1}^{n} AP_j^{(b)2}}} \quad \text{Eq. (1)}$$

where $\delta_{ij}=1$ if $AP_i=AP_j$ (i.e., their MAC addresses are the same), else 0.

If the received list of APs is not similar (per definition in Eq. (1)) to any of the entries in the database or if it is similar to some of the entries but the additional (other than Wi-Fi APs) features do not match, the app makes a new entry into the database. The location label for this new entry is obtained either through collaboration (which happens most of the times) or manually input by the user. A manual entry method may be greatly minimized using other techniques, such as: (1) using well-known Wi-Fi-location databases such as the Wireless Geographic Logging Engine (WiGLE) or other tool to obtain GPS coordinates and then location labels from Google Maps; (2) using a newer mobile Operating System (OS) such as Android OS or iOS that provides venue names (such as "San Francisco Airport") if published by access point using the ScanResult.venueName attribute. Further, to ensure uniformity among all labels and to remove ambiguity, various embodiments use an ontology based framework for assigning labels that takes user input and converts them into standard labels that are hierarchically defined (e.g., country, zip code, street, building number, room number/name, and so on). Each device thus maintains a database of location features and labels corresponding to locations it is associated with (i.e., visited at least once).

Figure 6:
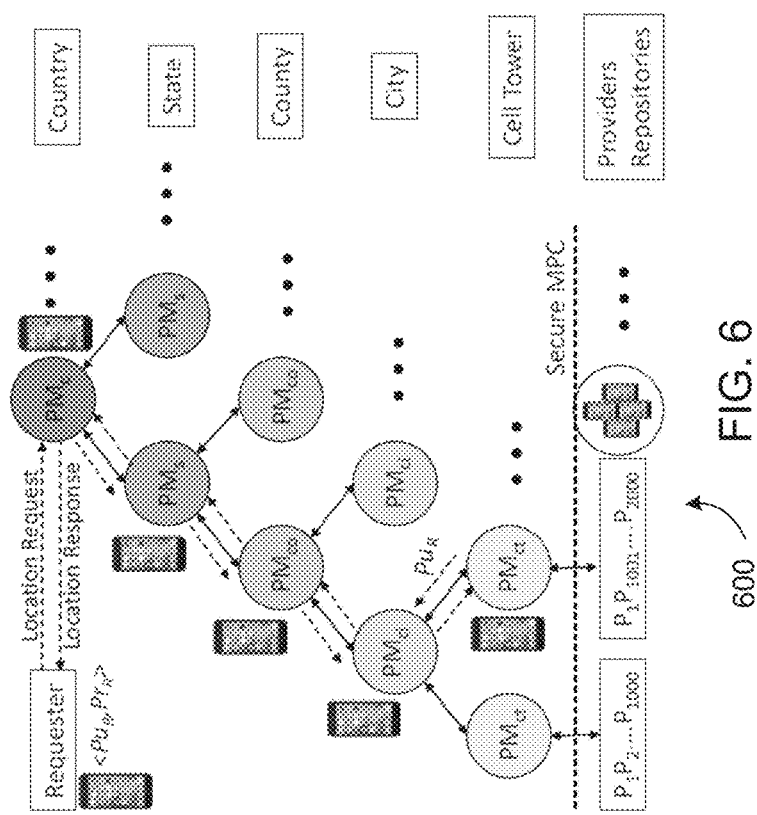
FIG. 6 graphically depicts a path taken by an example location request within a hierarchical The Onion Router (ToR) network according to an embodiment.

FIG. 6 graphically depicts a path taken by an example location request within a hierarchical TOR network according to an embodiment. Specifically, FIG. 6 graphically depicts a number of Phone Masters (PM) devices (i.e., UE also using the applications described herein) operating at different levels within a hierarchical TOR network and processing a location request according to a privacy enhanced path (shown in dashed arrows).

A location "requester" is a device that has these features but does not know the location label. A location "provider" is a device that is willing to query the location request over its database and provides a probability distribution over the location labels. The communication between the requester and providers is made anonymous using ToR routing employed on a hierarchical architecture ("country," "state," "county,", "city," and "cell tower."), as shown in FIG. 6. The ToR nodes that are involved in forwarding the traffic are called Phone Masters (PMs), which are also mobile phones that benefit from using the various embodiments. A PM stores the IDs of its children—for example a state level PM will store the IDs of its county level PMs and so on. The last level PM, viz., the Cell Tower PM (CTPM), however, stores the IDs of the providers who have agreed to receive location queries corresponding to that cell tower. A provider can choose to remain anonymous at one of the levels mentioned above. For example, if a user selects city-level anonymity, his/her device ID is included in the repositories of all the cell tower level PMs belonging to that city. This way, each user is empowered to choose a user-specific level of privacy. Note that there are multiple PMs at each level (executing the same function) for load balancing and avoiding single point of failure.

A location requester first contacts the top-level PM (country-level) with a location request. This request is forwarded continuously until it reaches the correct cell-tower PM. The cell-tower PM, upon receiving the request, picks j random devices ("providers") from its repository to respond to this query. Each collaborator queries its own database with these location features and generates a location distribution using the Inverse Euclidean Distance (IED) classifier, which is a two-step classifier that only considers those entries with non-zero similarity with the input Wi-Fi list as training data. In IED, given these non-zero similarity entries consisting of additional features and labels as well as a query entry, the various embodiments calculate the inverse of the Euclidean distance between the query feature value and training entries for each of the additional features. These inverse distances are then normalized to form probability distribution over the labels. Note that there will be as many such distributions as the number of additional features. These distributions and the distribution corresponding to Wi-Fi similarity measures are then fused using weighted average fusion to generate the output distribution. This distribution is then enlarged by adding $p_1$ number of random labels and perturbed by adding random noise n~ $\mathcal{N}(0,p_2)$, in proportion to the privacy needs of the provider. Such location distributions from all the collaborators are fused to generate the final result (here, only top k labels, in terms of probability values, are considered from each collaborator). The CTPM sends back this final distribution to the requester again using the same overlay network. Note that the database in each device will almost saturate after some time. This is because each user is usually associated with only a few places for most of the time. This drastically reduces the need for collaboration until the user visits new places. Hence, for most of the time, the location information is readily available for use in location-based services.

Various embodiments enhance the overall granularity of the embodiments described above by using an additional feature set; namely, geo-magnetic field data which the inventors note is stable in that it does not change with time of the day or day of the week, unlike light and sound levels, as it depends on the structure of the building, which is fixed after construction. The various embodiments may achieve granularities of the order of 1 m with this addition, which directly enhances the overall granularity of the solution provided by the various embodiments.

k-Anonymity-Based Infection Marking

In various embodiments, user-location is performed in a manner that avoids breaching the privacy of users. However, the embodiments takes an active step beyond user localization and makes recommendations regarding which locations the user should avoid at any specific time. It is noted that recommending users to avoid specific locations in real time could potentially jeopardize other users' privacy. For instance, imagine a room, occupied by one person only, is recommended against by the embodiments; one can conclude that the person in the room has a potential viral infection. the embodiments extend and leverage k-anonymity techniques to ensure that the users privacy is protected while making its recommendations. In particular, various embodiments define a recommendation to be k-anonymous if it does not disclose the identity of any group of people with fewer than 'k' individuals in it. For instance, a 2-anonymous recommendation will ensure that the identity of no single individual can be inferred (as discussed in the example above). The various embodiments ensure k-anonymity in the recommendation through two main mechanisms: (1) ensure that the target space/region in a recommendation is large enough to include at least k people; (ii) the recommendations will be calculated based on the target space's current and recent occupying individuals to avoid both direct person-to-person infection and aerosol transmission originated from the risky individuals who may have left the room already recently. Upon making a recommendation against a specific region in the building, a solution according to the various embodiments will not disclose to the user if the recommendation is made because of the people that occupy that space right now or in a recent history. The historical information regarding the room occupancies will enlarge the group of people considered in the embodiments' calculations and hence will allow to make recommendations against more specific smaller regions in the building. As an example, in a 5-anonymous setting, the embodiments may recommend against a frequently-used kitchen area (which is occupied by one person right now) without disclosing that individual's privacy, because the recommendation may have been made due to any of the 4 (i.e., 5-1) people in that kitchen recently.

ContTrace: Contact Tracing as a Core Disease Control Measure

ContTrace identifies the people who had been in contact with a particular person (say 'specimen') in the past two weeks, which is accomplished as follows. The database records (i.e., the locations and their sensor signatures) of specimen corresponding to the last two weeks are queried over the ToR network to identify devices whose databases have matching information in the last two weeks. When a device receives these query records, it initiates a comparison check to see if any of the query records are similar to the records in its database. If it is so, then the app alerts the user that s/he had been in potential contact with an infected person in the past two weeks and suggests the user to self-quarantine and contact the health provider. When this happens the app also presents the matching records (with sensor signatures including Wi-Fi, Cell ID, etc.) in its database that are similar with the query for user validation. In various embodiments, third party solutions may be used to perform the ContTrace function, and that the execution of the steps associated with this function may be provided by a third party app installed on the UE 201 or provided via a third party or remote server (e.g., servers 203 or 204).

Various embodiments provide an improved contact-tracing method that is robust against the following issues; (1) False Positives arising from close contact between individuals separated by walls and individuals who take precautions, such as the use of personal protective equipment, in their interactions with others or fleeting interactions, such as crossing paths in the grocery store, that are less likely to cause transmission; (ii) False Negatives arising from people not using a smartphone app according to the various embodiments, or not reporting positive status on the app even though they tested positive, or lingering of virus on surfaces/in air even after the specimen phone has left the area; (iii) Side channel attacks—correlate infected people with their pictures using a stationary camera connected to a Bluetooth device in a public place; (iv) Malicious use—falsely reporting several infections in a large geographical area for personal and political motives. Various embodiments use such as security auditing, bug bounties, and abusability testing to identify vulnerabilities and unintended consequences of the embodiments.

MobPred: Personalized and Group Behavior-Based Context & Mobility Prediction

In certain secure scenarios, it is not wise to rely solely on the context obtained from the phone's sensors (e.g., GPS and system clock to give location and time) because they could be hacked unknowingly to the user. For example, a software virus might change the clock to show different time or spoof the GPS to show different location. However, it is hard to hack a model (more so, a collaborative one) that is learned over a long period of time. Secondly, it is possible that context from sensors is noisy (due to malfunction) or does not contain enough information, e.g., no GPS on a table device. As such, it would be helpful if there were another way of obtaining this information such that it would complement the context from sensors. Thirdly, future context prediction is useful for various embodiments including a proactive recommendation system as it can pre fetch information/pre-plan based on the predicted context, and help the user plan future activities more efficiently and safely.

Figure 7:
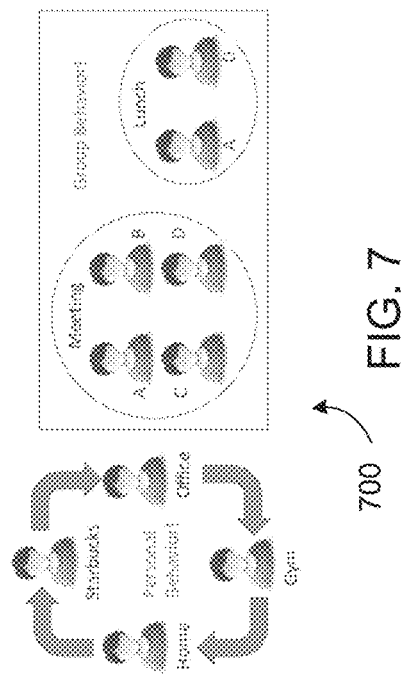
FIG. 7 graphically illustrates an exemplary user's personal behavior and group/collaborative filtering behavior.

Various embodiments use a personalized model (SelfContext) that predicts a user's context based on his/her past sequential history of contexts. FIG. 7 graphically illustrates an exemplary user's personal behavior and group/collaborative filtering behavior, such behaviors being applicable to user location prediction and user context at particular times. For example, a user's general routine during weekdays could be to head first to Starbucks near his home, then to his work and then to gym and back to home, as graphically depicted in FIG. 7. The learned model captures this behavior and may be used to validate the location of the user obtained via GPS at 5:30 pm to be at Gym (current context prediction) or provide recommendations ahead of time on the best route to take to go to Office (future context prediction).

Various embodiments obtain user context via two approaches; namely, sensors and personalized mode, such that an extra layer of confidence is added to the obtained context. However, the following situations are possible: contexts obtained from both approaches are very different, contexts from one of the approaches is not available (e.g., GPS may not be available) or insufficient leading to uncertainty. In such situations, assuming the user is closely connected to a group of other users, e.g., colleagues in the company as shown in FIG. 7 (right), gym friends, family members, etc.), it is possible that the context of other users in that group can provide additional information about the user's own context. Assume users A and D often go to meetings or have lunch together, refer to FIG. 7 (right). Now, if it is known that D is going to "Restaurant 1" tomorrow for lunch, it is most likely that the context of user A tomorrow around 1 pm is "having lunch with D at Restaurant 1" without having to rely on A's phone sensors at that instant. Exploring this aspect of context to provide a second layer of confidence to the context (over and above the personalized model), various embodiments may use such context as obtained through collaborative filtering of the contexts of users closely related to the primary user (GroupContext).

Figure 8:
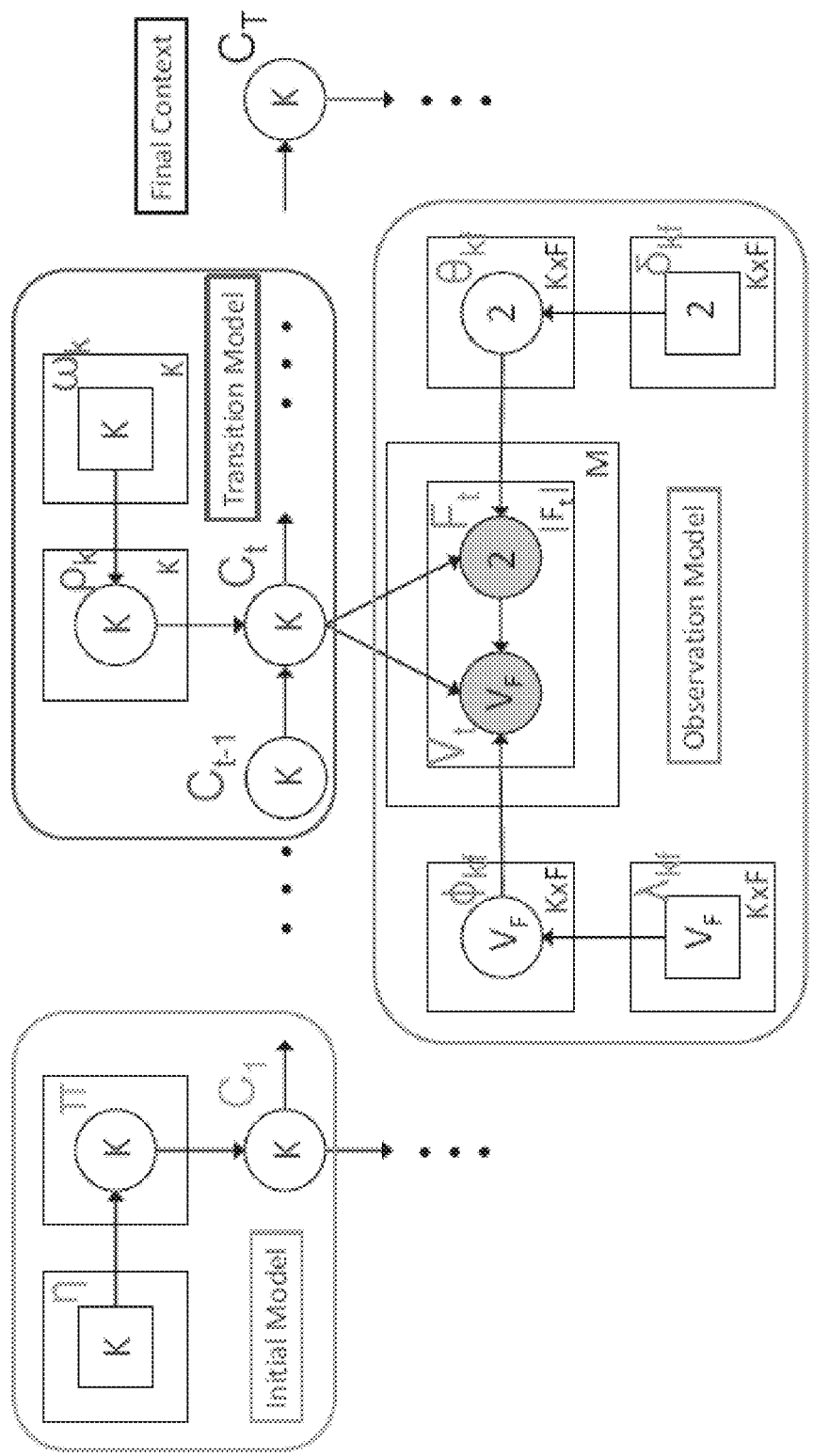
FIG. 8 graphically depicts a GroupContext model suitable for use in the various embodiments.

FIG. 8 graphically depicts a GroupContext model suitable for use in the various embodiments. Specifically, a GroupContext model may be provided by designing a novel emission model of a Hidden Markov Model (HMM) taking into account the multi-user collaborative filtering aspects as well as the unique features of the user context and details such as feature unavailability, e.g., GPS is not available indoors.

Referring to FIG. 8, context ($C_t$) is modeled as a latent variable in the HMM. For a given user, the observation corresponding to a context state at time t will be called context observations ($O_t$). Each observation, $O_t$, consists of a set of contextual feature-value pairs, e.g., location, time, foreground app, etc. These observations are obtained at regular time intervals (e.g., a minute to four hours). It is assumed that K number of latent context states spans across these T observations. Considering users u=1, ..., M, each user has a similar set of T observations.

Referring to FIG. 8, F is the total number of features, $V_F$ denotes the total number of possible values for feature F, $|F_t|=|V_t|$ denotes the number of features observed at time t, M is the number of users, and K is the number of hidden context states. For a GroupContext model for M users, the number of different categorical values a random variable (r.v.) can take is shown inside the circle or rectangle. A circle is used for a r.v., while a rectangle is used for hyperparameters. Observable variables are shaded. The number of repetitions of a rectangular block is shown at its bottom right corner. For a given user u, the observation at time t, $O_{tu}$ is a set of feature-value pairs, as shown in the following:

$$O_{tu}=(f_{tu},v_{tu})=(f_{t,u,i},v_{t,u,i})_{i=1}^{|f_{tu}|},$$

where $|f_{tu}|$ is the number of available features of user u, at time t.

Initial State Model: A prior distribution of contexts, π, is generated from prior Dirichlet distribution, η. $C_1$ is generated from π. It is assumes that a total of K possible context states for GroupContext over all M users.

Transition Model: A prior transition distribution of contexts, $\rho_{c_{t-1}}=\rho_k$, is generated from a prior Dirichlet distribution, $\omega_k$. $C_t$ is then generated from $\rho_{c_{t-1}}$ for a given $C_{t-1}$. Note that $\rho_k$ and $\omega_k$ can take K categorical values ($C_t$, current state) for each k ($C_{t-1}$, previous state).

Novel Emission Model: For $O_t$ generation under each $C_t$, since features are not always available (e.g., GPS is not available indoors), various embodiments will define a separate distribution for features ($F_t$) to account for their availability and then another distribution to obtain the values ($V_t$) for those features at time t, as illustrated in FIG. 8. $F_t$ is dependent on $C_t$, whereas $V_t$ is dependent on both $C_t$ and $F_t$. An initial feature distribution, $\theta_{c_t,f_t}=\theta_{k,f}$, is generated from a prior Dirichlet distribution, $\delta_{k,f}$. Feature $F_t$ is then generated from $\theta_{k,f}$, which can take two categorical values—whether the feature is present or not for the given context, $c_k$. It is assumed that a total of F possible features over all observations of all users. A prior value distribution, $\phi_{c_t,f_t}=\phi_{k,f}$, is generated from a prior Dirichlet distribution, $\lambda_{k,f}$. Value $V_t$ is then generated from $\phi_{c_t,f_t}$ for a given context $c_t$ and feature $f_{t,i}$. For a given feature f, it is assumed that V can take $V_f$ possible values. The priors will be chosen such that the summation and non-negativity constraints on the parameters be satisfied and also to encode prior information. For example, if it is known that a user frequently moves between two known points, the prior parameter for this transition, $\omega_k$, is given a high value. Training the HMM involves finding the parameters Ψ that maximize the likelihood.

Given the complex nature of the likelihood expression, it is very difficult to derive a closed-form solution of Ψ. Hence, it is proposed to solve this using a custom variant of an iterative approach called Expectation Maximization (EM). As to run the EM algorithm requires gathering the observation data of different users at a single place (which may pose privacy concerns), the various embodiments use a method devised to achieve this in a privacy-preserving manner using standard Homomorphic encryption techniques. The embodiments then use the learned parameters to predict the future observations given past observations. The embodiments do this by first finding the distribution over future states, and then by multiplying the distribution over the observations given the future state.

In the above models, it is assumed that the number of hidden contexts K is given; however, in general, this number needs to be determined automatically from the user data. To determine the best K within some known range, $\mathcal{K}_{range}$, various embodiments define a metric, called Perplexity, that determines how well the chosen K fits for prediction tasks over the testing set. Finding such metric involves calculating the prediction probability over a sequence of observations given a sequence of past observations from the testing set. Specifically, Perplexity may be defined as follows:

$$\text{Perplexity} = \exp\left(-\frac{\log p(o_{t+1:T}|o_{1:t})}{\sum_{u=1}^{M}\sum_{k=t+1}^{T}|o_{tu}|}\right),$$

where $|o_{tu}|$ is the number of features observed at time t for user u.

Intuitively, a small Perplexity is desired. Although in general the Perplexity reduces as K increases, a large K is not preferred due to the risk of overfitting. Hence, there is a tradeoff between the two extremes. (b) Improvements to a brute-force approach may be realized by finding the most closely related users in a group and prioritizing the processing of these users such that a sufficiently accurate result is achieved. For example, various embodiments prioritize the processing of members of groups including the modeled user based upon a level of correlation between group members and the use, such correlation being determine with respect to time/location connections and/or other contextual information.

Recommend: Optimized Risk Assessment and Recommendations

The last software module, Recommend, takes the outputs of the previous modules and performs risk assessment to generate the recommendations to the user. Recommend models the problem as a convex optimization and solves for the solution using a variety of powerful techniques including mixed integer non-linear programming. A simple and lean approach for this is as follows. Recommend first gathers the route/place information along with the intensity markings obtained from previous modules. It then tries to find all the possible combinations satisfying the problem at hand (e.g., all routes from place A to B) along with their combined average marking intensity and any additional cost information (i.e., time taken to follow the route). It then displays all possible solutions in decreasing order of marking intensity (e.g., using three colors such as red, green, and blue) along with additional cost information such as time taken to follow the route. The user can then choose the option that best fits his/her requirements. In this way, the various embodiments provide the users with valuable information and puts the users in a position to make the best decision for themselves.

App Interface: Various embodiments use a design that is visually appealing and provides an easy-to-understand interface for the app, so that persons of all ages can understand and follow the recommendations provided by your app. In order to enhance user-friendliness, various embodiments further use additional software add-ons such as from Google Maps (or similar) and/or local information to assist the user in inputting the information easily (e.g., source and destination addresses).

Various embodiments provide improved performance by ensuring that the following properties of convex optimization are satisfied when the problem is formulated; (i) every local minimum is a global minimum; (ii) the optimal set is convex; (iii) if the objective function is strictly convex, then the problem has at most one optimal point. To solve the convex optimization problem, various embodiments may leverage Bundle methods and Subgradient methods, among others, with the primary goal being able to compute the solutions in reasonable time on resource-limited hardware. Various embodiments specifically focus on Subgradient methods as they can be implemented simply and are also widely used. Secondly, various embodiments use modeling the problems as Constraint Satisfaction Problems (CSPs), which are mathematical questions defined as a set of objects whose states/values must satisfy a number of constraints or limitations. For this purpose, the various embodiments may leverage techniques such as Constraint Programming (CP), Boolean Satisfiability Problem (SAT), Satisfiability Modulo Theories (SMT), Mixed Integer Programming (MIP), and Answer Set Programming (ASP).

The above-described embodiments advantageously enable proactively advising users away from specific locations based on previously collected information regarding whether (potentially) infected individuals are or have been in those places recently. By contrast, existing contact-tracing solutions notify the users about their potential exposures after it has happened (e.g., because they require two phones to be in proximity for Bluetooth signal cross-transformation), when in fact it may be too late for the individual already. The above-described embodiments notify the users before a potential exposure based on its user localization, behavioral modeling, and prediction capabilities. Furthermore, the various embodiments do not require energy-expensive sensors such as Bluetooth and GPS to be on; rather, the embodiments achieve their purpose with the UE Wi-Fi signals that are already in place, thereby providing a low performance overhead (and low battery consumption). Various embodiments provide accurate localization outcomes while preserving the privacy of the individual users completely using underlying distributed cryptographic guarantees. In summary, the various embodiments overcome many disadvantages of existing approaches; the DP4coRUna App provides proactive recommendations that put the user in charge of decision making at every time step. Also, the various embodiments work both indoor and outdoor (as it leverages Wi-Fi, Cell ID, light and sound levels, etc.), has built-in privacy and security features, and works in a scalable distributed manner.

Further embodiments advantageously enable proactively advising users away from specific locations based on previously collected information regarding whether dangerous human activity (e.g., criminal activity), industrial activity (e.g., toxic spills or other pollution), weather activity (e.g., flooding or other dangerous weather situations), or animal activity (e.g., animal infestation or predator attacks) is or has been associated with such places recently.

By overlaying/using crime statistic information with the mapping information, users may be guided around areas known to be dangerous at certain times of the day, on certain days, and so on.

By overlaying/using weather information with the mapping information, users may be guided around areas known to be currently dangerous or expected to be dangerous, such as from flash flooding, tornados, or other weather-related events.

Although various embodiments which incorporate the teachings of the present invention have been shown and described in detail herein, those skilled in the art can readily devise many other varied embodiments that still incorporate these teachings. Thus, while the foregoing is directed to various embodiments of the present invention, other and further embodiments of the invention may be devised without departing from the basic scope thereof

What is claimed is:

1. A location safety management method configured for use by each of a plurality of cooperating mobile devices, the method comprising:
  at a mobile device within the plurality of cooperating mobile devices and configured to communicate via one or more networks, receiving from at least one other mobile device within the plurality of cooperating mobile devices data indicative of infectious locations proximate the mobile device and adding the received infectious locations data to an infectious location dataset stored locally at the mobile device;
  at the mobile device, in response to receiving an infectious locations request from another mobile device, confidentially transmitting at least a portion of the locally stored infectious location dataset toward the requesting mobile device;

at the mobile device, in response to a need for updated infectious locations data, confidentially transmitting a hierarchically-descriptive infectious locations request toward at least one other mobile device within the plurality of cooperating mobile devices;

at the mobile device, in response to receiving a response to the hierarchically-descriptive infectious locations request, adding any received data indicative of infectious locations to the infectious location dataset stored locally at the mobile device; and at the mobile device, using the infectious location dataset to adapt operation of a navigation application operable at the mobile device to display infectious locations proximate the mobile device.

2. The method of claim 1, further comprising:
at the mobile device, time-stamping received data indicative of infectious locations proximate the mobile device prior to adding the received infectious locations data to the infectious location dataset stored at the mobile device.

3. The method of claim 1, further comprising:
at the mobile device, using the infectious location dataset to adapt operation of the navigation application operable at the mobile device to reduce a number of infectious locations associated with a recommended route.

4. The method of claim 1, further comprising:
at the mobile device, receiving a recommended route from the navigation application operable at the mobile device; and
generating an alert indicative of the recommended route including an infectious location.

5. The method of claim 1, further comprising:
at the mobile device, using the infectious location dataset to identify infectious public conveyance seating locations.

6. The method of claim 1, further comprising:
at the mobile device, monitoring location information associated with the mobile device to build thereby a user routing behavior model configured to correlate recent location history of the mobile device to a prior route; and
at the mobile device, generating an alert indicative of recent location history of the mobile device being correlated to a prior route including an infectious location.

7. The method of claim 6, wherein the user routing behavior model includes contextual attributes associated with personal and group behaviors of a user of the mobile device.

8. The method of claim 6, wherein confidentially transmitting the hierarchically-descriptive infectious locations request toward at least one other mobile device within the plurality of cooperating mobile devices is performed in response to a determination that current user movement of the mobile device is associated with a route defined within the routing behavior model.

9. The method of claim 6, further comprising:
at the mobile device, determining via a recommendation module at least one alternate route in response to user travel via a respective user profile route having intermediate locations associated with infection level exceeding a threshold level;
wherein each alternate route comprises an alternate sequence of intermediate locations selected to provide reduced infection exposure to the user, wherein the recommendation module is configured to transmit the at least one alternate route toward a user presentation device configured to graphically present the user profile route and any determined alternate route.

10. The method of claim 9, wherein at least some of the intermediate locations comprise indoor locations defined by at least one of room identifier, floor number, floor location, and a place identifier.

11. The method of claim 9, wherein an intermediate location associated with infection level exceeding a threshold level comprises a location predicted to be occupied by an infected person prior to user arrival at the location.

12. The method of claim 2, wherein the time-stamped infection level for a location comprises at least one of a presence of an infected person at the location, a presence of an infected person at the location within a predefined time period, a presence of a threshold number of infected persons at the location, and a presence of a threshold number of infected persons within a predefined distance proximate the location.

13. The method of claim 2, wherein infection level for a location associated with an infected person is generated via a k-anonymity mechanism configured to avoid specifically identifying the infected person.

14. The method of claim 2, wherein the time-stamped infection level for a location comprises at least one of data indicating that a location requires cleaning and data indicating that a location will require cleaning before the user reaches the location.

15. The method of claim 2, wherein the time-stamped infection level for a location is associated with a persistence value indicative of an amount of time after infection that the location will remain infectious.

16. The method of claim 1, wherein confidential transmission is performed using a privacy-enhanced communications protocol.

17. The method of claim 1, further comprising:
at the mobile device, periodically confidentially transmitting a hierarchically-descriptive infectious location request toward the plurality of cooperating mobile devices; and
in response to receiving a response to the hierarchically-descriptive infectious location request, adding any received infectious locations data to the infectious location dataset stored at the mobile device.

18. The method of claim 7, wherein the user routing behavior model is improved over time via a sequence of observations associated with the user of the mobile device and a sequence of observations associated with members of groups including the user of the mobile device, wherein the sequence of observations associated with the members of groups including the user are processing in a prioritized manner based upon a level of correlation of group members to the user.

19. A location safety management system implemented via a plurality of cooperating mobile devices, each mobile device comprising:
a processor and a memory for storing computer instructions which, when executed by the processor, cause the mobile device to perform:
at a mobile device within the plurality of cooperating mobile devices and configured to communicate via one or more networks, receiving from at least one other mobile device within the plurality of cooperating mobile devices data indicative of infectious locations proximate the mobile device and adding the received infectious locations data to an infectious location dataset stored locally at the mobile device;

at the mobile device, in response to receiving an infectious locations request from another mobile device, confidentially transmitting at least a portion of the locally stored infectious location dataset toward the requesting mobile device;

at the mobile device, in response to a need for updated infectious locations data, confidentially transmitting a hierarchically-descriptive infectious locations request toward at least one other mobile device within the plurality of cooperating mobile devices;

at the mobile device, in response to receiving a response to the hierarchically-descriptive infectious locations request, adding any received data indicative of infectious locations to the infectious location dataset stored locally at the mobile device; and at the mobile device, using the infectious location dataset to adapt operation of a navigation application operable at the mobile device to display infectious locations proximate the mobile device.

20. A non-transitory computer readable storage medium storing instructions which, when executed by a computer, adapt operation of the computer to provide a location safety management method configured for use by each of a plurality of cooperating mobile devices, the method comprising:

at a mobile device within the plurality of cooperating mobile devices and configured to communicate via one or more networks, receiving from at least one other mobile device within the plurality of cooperating mobile devices data indicative of infectious locations proximate the mobile device and adding the received infectious locations data to an infectious location dataset stored locally at the mobile device;

at the mobile device, in response to receiving an infectious locations request from another mobile device, confidentially transmitting at least a portion of the locally stored infectious location dataset toward the requesting mobile device;

at the mobile device, in response to a need for updated infectious locations data, confidentially transmitting a hierarchically-descriptive infectious locations request toward at least one other mobile device within the plurality of cooperating mobile devices;

at the mobile device, in response to receiving a response to the hierarchically-descriptive infectious locations request, adding any received data indicative of infectious locations to the infectious location dataset stored locally at the mobile device; and at the mobile device, using the infectious location dataset to adapt operation of a navigation application operable at the mobile device to display infectious locations proximate the mobile device.

21. The method of claim 7, wherein:

data indicative of infectious locations further includes data indicative of unsafe locations; and the infectious location dataset further includes unsafe location data.

22. The method of claim 21, wherein unsafe location data comprises data indicative of unsafe human activity.

23. The method of claim 21, wherein unsafe location data comprises data indicative of at least one of unsafe industrial activity, unsafe weather activity, and unsafe animal activity.

* * * * *